United States Patent [19]

Jochum et al.

[11] Patent Number: 4,542,172

[45] Date of Patent: Sep. 17, 1985

[54] DENTAL CEMENT CONTAINING POLYVINYL BUTYRAL AS AN ADDITIVE

[75] Inventors: Peter Jochum, Hechendorf; Oswald Gasser, Seefeld, both of Fed. Rep. of Germany

[73] Assignee: ESPE Fabrik Pharmazeutischer Praparate GmbH, Fed. Rep. of Germany

[21] Appl. No.: 486,997

[22] Filed: Apr. 21, 1983

[30] Foreign Application Priority Data

May 7, 1982 [DE] Fed. Rep. of Germany ....... 3217259

[51] Int. Cl.$^4$ ................................................ A61K 6/08
[52] U.S. Cl. ........................................ 523/116; 106/35; 106/119; 260/998.11; 433/199.1; 433/228.1; 524/6; 524/291; 524/436
[58] Field of Search ...................... 106/119, 35; 524/2, 524/4, 6, 433, 436, 291; 523/116; 433/199, 228; 260/998.11

[56] References Cited

U.S. PATENT DOCUMENTS 3,047,408  7/1962  Dougherty ........................... 560/71
4,272,292  6/1981  Mizuno et al. ........................ 106/22

Primary Examiner—Lorenzo B. Hayes
Attorney, Agent, or Firm—Bacon & Thomas

[57] ABSTRACT

Polyvinyl butyral with a degree of acetalization of at least 75% is added to a dental cement on basis of calcium hydroxide and salicyclic esters of aliphatic alcohols. By this additive improved water resistance and increased compressive strength upon hardening are imparted to the dental cement. The obtained dental cement furthermore has strongly alkaline pH value, so that an effective protection of the pulp can be achieved and formation of a secondary dentin layer is stimulated. In the common formulation of the materials for the dental cement in form of two separate mixing components the polyvinyl butyral can be added either to the mixing component containing the salicylic acid ester or to the mixing component containing the calcium hydroxide, or also to both components.

10 Claims, No Drawings

DENTAL CEMENT CONTAINING POLYVINYL BUTYRAL AS AN ADDITIVE

The invention relates to a dental filling composition on basis of calcium hydroxide and salicylic acid esters suited for linings in a tooth cavity and for pulp cappings. Due to the toxicity of most of the common fillings linings are necessary in case of rather deep tooth cavities and, in particular, when a pulp capping becomes necessary.

For some time already dispersions of calcium hydroxide in water or in aqueous or organic solutions of film-forming materials have been used for the treatment of tooth cavities, since calcium hydroxide on the one hand protects the pulp against the attack of acids from the fillings and on the other hand stimulates the formation of secondary dentin.

When calcium hydroxide dispersions in aqueous or organic systems are used, there is not obtained, however, a cavity lining of sufficient mechanical strength protecting the tooth from being affected by the mechanical impact and stress during the filling operation.

For overcoming this difficulty U.S. Pat. No. 3,047,408 describes a dental filling composition comprising powdery calcium hydroxide and esters of polyhydric alcohols with salicylic acid as well as optionally methyl salicylate, powdered insert fillers and/or plasticizers. This dental cement has all advantages of the calcium hydroxide dispersions, i.e. it causes the formation of secondary dentin and acts, by its high pH value of more than 11, as a protective barrier against acids and other toxic substances contained in some filling materials. Due to the presence of salicylic acid esters the cement hardens rapidly after placement into the tooth cavity to provide a base that protects the tooth pulp during the subsequent filling operation.

A further dental cement for a cavity lining consisting of calcium hydroxide and a salicylic acid ester of a monohydric alcohol is described in Swiss Pat. 610,199. Linings produced of this cement have a relatively poor compressive strength.

It has been found, however, that, although dental cements on basis of calcium hydroxide and salicylic acid esters have in fact the mentioned advantageous properties shortly after they have been applied, they are however quite soluble in water and consequently are washed out.

This disadvantageous effect is described for example in The Journal of the British Dental Association, 147 (5) 1979, page 111.

Investigations made by the applicant have confirmed that the cement produced according to U.S. Pat. No. 3,047,408 decomposes within a relatively short time when stored in water.

It has been known to add paraffin oil or linseed oil to cements on basis of salicylic acid esters in an effort to reduce the solubility in water. While resistance to water is in fact improved by these additives, a pH value of less than 10 is obtained however, whereby the advantageous protection of the pulp gets lost. In all attempts to produce a cement containing calcium hydroxide known so far high pH-value and water-resistance are mutually exclusive.

The dental cements on basis of calcium hydroxide and salicylic acid esters are usually obtained of two pastes: One so-called salicylic ester paste, the main component of which is a mixture of various salicylic esters with inert fillers, and one so-called calcium hydroxide paste, which contains as main constituent calcium hydroxide in a liquid paste base.

A further disadvantage of the calcium hydroxide cements common so far is the separation of the pasty component containing the esters before its application.

It is an objective of the invention to provide a dental cement on basis of calcium hydroxide and salicylic acid esters of aliphatic alcohols having a sufficiently high pH value and favouring formation of secondary dentin and therefore completely fulfilling its function as protective barrier against acids and other toxic substances, which has however on the other hand good resistance to water and increased compressive strength, guaranteeing thereby a durable protection of the pulp. It has been found that this objective may be attained by adding polyvinyl butyral to a dental cement on basis of salicylic acid esters and calcium hydroxide.

Polyvinyl butyral is known as binding agent in rubber print colours and lacquers. It could however not be expected regarding this known use that the addition of polyvinyl butyral to a calcium hydroxide cement, as according to the invention, would improve the characteristics of the latter.

The subject matter of the present invention is a dental composition consisting of two separate mixing components, wherein one mixing component (a) contains salicylic acid esters of aliphatic alcohols and the other mixing component (b) contains calcium hydroxide which is characterized by the fact that one of the mixing components or both of the mixing components additionally contain a polyvinyl butyral having a degree of acetalization of at least 75%.

The dental cements obtained according to the invention by the use of polyvinyl butyral have a reduced solubility in water and, after hardening, have increased compressive strength. Further the pH value remains strongly alkaline, so that an effective protection of the pulp can be achieved and the formation of secondary dentin is stimulated. The addition of polyvinyl butyral made according to the invention further helps to make the ester paste, i.e. the mixing component for the dental cement containing the salicylic acid ester, resistant against separation.

Apart from the feature of the addition of polyvinyl butyral, the cement composition corresponds to that of known salicylic acid ester-calcium hydroxide dental cements as described for example in U.S. Pat. No. 3,047,408 and in the similar German "Auslegeschrift" 12 02 937. One of the main components is calcium hydroxide, which is preferably present in stoichiometric excess over the salicyclic acid ester(s).

A further essential component is a salicylic acid ester of a monohydric or polyhydric alcohol, preferably an aliphatic alcohol having 1 to 8 carbon atoms, in particular of such a dihydric or trihydric aliphatic alcohol, having preferably 3–8 carbon atoms.

Mixtures of two or more different such esters may be used. According to a preferred embodiment salicylic acid esters of polyhydric alcohols having 3 to 8 carbon atoms together with salicylic acid esters of monohydric aliphatic alcohols having 1 to 4 carbon atoms, in particular methyl esters or ethyl esters, are used.

A particularly preferred embodiment comprises a mixture of the salicylic acid monoester and -diester of 1,3-butane diol and salicylic acid methyl ester.

The dental cement may further contain customary inert fillers, such as titanium dioxide, tin dioxide, calcium sulfate, calcium phosphate, aluminum oxide, silica or zinc oxide, moreover pigments, X-ray contrast agents, such as barium sulfate or calcium tungstate, plasticizers and other additives customary for filling materials, such as e.g. zinc stearate, may be present.

According to the invention the polyvinyl butyral added is advantageously admixed in an amount of 0.2 to 5% by weight, preferably 0.5–2% by weight, based on the weight of the ester(s). It has a degree of acetalization of at least 75% and preferably at least 80% or more. The degree of polymerisation is 20–70, preferably 50–70.

Commercially available polyvinyl butyral, as described for example in the firm's publication of Farbwerke Hoechst AG "Mowital B" under the designations Mowital B 20 H, Mowital B 30 H and Mowital B 60 HH, is suited for the purposes of the invention. Of course also other commercially available products are suitable, as long as the desired degree of acetylization is achieved.

The basic materials for the production of a dental cement on basis of salicylic acid esters and calcium hydroxide are produced and sold according to a preferred embodiment as two paste-system: One calcium hydroxide paste and one salicylic ester paste, which are mixed shortly before being used. The hardening takes place by penetration of moisture, which is sufficiently available in the mouth, the hardening being accelerated by the body temperature.

The calcium hydroxide paste contains as is known calcium hydroxide as main component. Additionally inert fillers, such as titanium dioxide, tin dioxide, calcium sulfate, -phosphate, aluminum oxide, silica and zinc oxide, disinfectants, surface active substances such as for example zinc stearate, and as liquid base a plasticizer, such as for example ethyl toluene sulfonamide, may be present.

The ester paste can consist of a mixture of the salicylic acid esters, insert fillers, such as titanium dioxide, tin dioxide, calcium phosphate, aluminum oxide, silica, zince oxide etc., and an X-ray opaque agent, such as for example calcium tungstate.

Optionally both pastes may additionally contain pigments. The polyvinyl butyral according to the invention is preferably admixed to the ester paste, since in case of use of fillers in this paste it essentially prevents the separation of liquid and solid substance. Principally, however, the polyvinyl butyral can be added to any of the two components or also can be added to both of the two components.

It is further possible, but not necessary that a very small amount of calcium hydroxide, e.g. about 0.05 to approximately 1.5 % by weight, based on the salicylic esters, is added to the paste component containing the salicylic esters, in order to control its consistency. The essential part of the calcium hydroxide, however, is contained in the above-defined mixing component (b).

EXAMPLE 1

Preparation of the ester paste 0.8 g polyvinyl butyral, highly acetalized (degree of acetalysation about 82%), is dissolved in a mixture of 78 g 1,3-butane diol disalicylic acid ester (diester), 12.9 g 1,3-butane diol monosalicylic acid ester (monoester) and 8.4 g salicylic acid methyl ester. 39.9 g of this solution are mixed with 60.7 g of a powder mixture of 0.6 g calcium hydroxide, 15.2 g calcium tungstate and 45.1 g titanium dioxide to form a paste.

Preparation of the calcium hydroxide paste 40.7 g calcium hydroxide are mixed with 8.2 g zinc oxide, 4.5 g titanium dioxide, 0.3 g zinc stearate, 7 g silicic acid and 39.4 g ethyl toluene sulfonamide to form a paste.

Preparation of the dental cement

Equal volumes of ester paste and calcium hydroxide paste are processed to form a dental cement-like mixture, which, after hardening at 100% relative air humidity and 36° C., has the physical properties set out in the table.

COMPARATIVE EXAMPLE 1

A dental cement is prepared from the same components as in example 1, the addition of polyvinyl butyral being omitted however. The physical properties of the obtained, hardened cement are measured in the same manner as in example 1 and are stated in the table.

EXAMPLE 2

Preparation of the ester paste

In a mixture of 77.8 g diester (same as example 1), 12.85 g monoester (same as example 1) and 8.54 g salicylic acid methyl ester there is dissolved 0.8 g polyvinyl butyral (degree of acetalization about 82%). 39.3 g of this solution are processed to form a paste together with 60.7 g of a powder mixture of 0.6 g calcium hydroxide, 15.1 g calcium tungstate and 45 g aluminum oxide.

Preparation of the dental cement

Equal volumes of this ester paste are processed together with a calcium hydroxide paste according to example 1 to form a dental cement-like mixture, which after hardening has properties comparable to those of the cement of example 1.

EXAMPLE 3

Preparation of the ester paste 79 g diester (same as example 1), 12.9 g monoester (same as example 1) and 8.5 g salicylic acid methylester are mixed.

39.1 g of this solution are processed to form a paste with 45.1 g of titanium dioxide, 15.2 g of calcium tungstate and 0.6 g of calcium hydroxide.

Preparation of the calcium hydroxide paste 40.7 g of calcium hydroxide are processed with a solution of 0.8 g polyvinyl butyral (Mowital B 60 HH) in 43.3 g N-ethyl-(o,p)toluene sulfonamide and 8.2 g zinc oxide, 0.25 g zinc stearate, 2.3 fumed silica and 4.5 g titanium dioxide to form a paste.

Preparation of the dental cement

Equal volumes of the two pastes are mixed. After hardening at 100% rel. air humidity and 36° C. a cement suitable as water-proof, alkaline cavity lining is obtained.

EXAMPLE 4

Preparation of the ester paste 2.4 g polyvinyl butyral are dissolved in a solution of 76.7 g of diester (same as example 1), 12.6 g of monoester (same as example 1) and 8.3 g of salicylic acid methyl ester.

39.1 g of this solution are processed with a powder mixture of 45.1 g of titanium dioxide, 15.2 g of calcium tungstate and 0.6 g of calcium hydroxide to form a pasty composition.

Preparation of the dental cement

By mixing one part by volume of this paste with one part by volume of the calcium hudroxide paste according to example 1 a cement having the properties stated there is obtained.

EXAMPLE 5

Preparation of the ester paste 1.2 g highly acetalized polyvinyl butyral (degree of acetalization approximately 82 %) are dissolved in a mixture of 78 g of diester (see example 1), 12.9 g of monoester (see example 1), 13.8 g trimethylol propane-tris-salicylic acid ester and 8.4 g salicylic acid methyl ester.

22 g of this mixture are mixed with a powder mixture of 0.3 g of calcium hydroxide, 7.6 g calcium tungstate and 22.6 g titanium dioxide to form a homogeneous paste.

Preparation of the dental cement

One part by volume of this ester paste is processed with one part by volume of the calcium hydroxide paste produced in example 1 to form a homogeneous cement, which after its hardening has favourable properties as cement for cavity linings.

EXAMPLE 6

Preparation of the ester paste 38.6 g of the solution of polyvinyl butyral in the mixture of salicylic acid esters according to example 2 are processed into a paste by admixture of 14.8 g calcium tungstate, 0.6 g calcium hydroxide, 44.1 g tin dioxide and 2.0 g fumed silica.

Preparation of the dental cement

By mixing one part by volume of this paste with one part by volume of the calcium hydroxide paste according to example 1 a cement having the properties stated there is obtained.

TABLE

| example | additive | compressive strength (1) (kp/cm$^2$) | period until compressive strength unmeasurable (2) (weeks) | solubility 24 h in H$_2$O (mg) | separation of the ester paste into its components |
|---|---|---|---|---|---|
| example 1 | 0.8% polyvinyl butyral (Mowital B60 HH) | 260 | >24 | 7,5 | none |
| comparative example 1 | without additive | 100 | 6 | 19 | clear separation |

(1): after having been stored at 36° C. and 100% relative humidity for 24 hours
(2): immersed in water at 36° C. until dissolution

We claim:

1. A preparation which on mixing forms a dental cement comprising two separate mixing components, one mixing component (a) containing at least one salicylic ester of an aliphatic alcohol; said alcohol selected from the group consisting of aliphatic monohydric alcohols, aliphatic polyhydric alcohols and mixtures thereof; and the other mixing component (b) containing calcium hydroxide, characterized in that one of the mixing components or both mixing components additionally contain a polyvinyl butyral having a degree of acetalization of at least 75%.

2. The composition of claim 1, characterized in that the polyvinyl butyral has a degree of acetalization of at least 80%.

3. The composition of claims 1 or 2, characterized in that the aliphatic alcohols are polyhydric.

4. The composition of claims 1 or 2, characterized in that mixing component (a) contains a mixture of salicylic esters of monohydric and polyhydric alcohols.

5. The composition of claim 1, characterized in that 0.2 to 5% by weight of polyvinyl butyral, based on the weight of salicylic acid ester, is added.

6. The composition of claim 2, characterized in that 0.2 to 5% by weight of polyvinyl butyral, based on the weight of salicylic acid ester, is added.

7. The composition of claim 3, characterized in that 0.2 to 5% by weight of polyvinyl butyral, based on the weight of salicylic acid ester, is added.

8. The composition of claim 4, characterized in that 0.2 to 5% by weight of polyvinyl butyral, based on the weight of salicylic acid esters, are added.

9. A method of preparing a dental cement, which comprises mixing a two-component mixing preparation, one mixing component (a) containing salicylic esters of aliphatic alcohol, and the other mixing component (b) containing calcium hydroxide, wherein one of the mixing components or both mixing components additionally contain a polyvinyl butyral having a degree of acetalization of at least 75% to form a paste; forming the paste into the desired shape and permitting it to cure.

10. A dental cement prepared according to the method of claim 9.

* * * * *